United States Patent [19]

Lacroix et al.

[11] Patent Number: 5,932,775
[45] Date of Patent: Aug. 3, 1999

[54] PROCESS FOR STABILIZATION OF PENTAFLUOROETHANE

[75] Inventors: Eric Lacroix, Amberieux d'Azergues; Jean-Marc Sage, Oullins, both of France

[73] Assignee: Elf Atochem S.A., France

[21] Appl. No.: 08/963,759

[22] Filed: Nov. 4, 1997

[30] Foreign Application Priority Data

Nov. 4, 1996 [FR] France .................................. 96 13400

[51] Int. Cl.⁶ ..................................................... C07C 17/42

[52] U.S. Cl. .......................... 570/122; 570/103; 570/111; 570/114; 570/116

[58] Field of Search ...................................... 570/103, 111, 570/114, 116, 122

[56] References Cited

U.S. PATENT DOCUMENTS

| 2,797,250 | 6/1957 | Copelin .................................... 570/111 |
| 4,045,503 | 8/1977 | Hutson, Jr. et al. . |

FOREIGN PATENT DOCUMENTS

| 538085A1 | 4/1993 | European Pat. Off. . |
| 539719A1 | 5/1993 | European Pat. Off. . |
| 539720A1 | 5/1993 | European Pat. Off. . |
| 539720B1 | 1/1996 | European Pat. Off. . |
| 538085B1 | 4/1996 | European Pat. Off. . |
| 539719B1 | 6/1996 | European Pat. Off. . |
| 2682377 | 4/1993 | France . |
| 1335618 | 10/1973 | United Kingdom . |

*Primary Examiner*—Alan Siegel
*Attorney, Agent, or Firm*—Bell, Boyd & Lloyd

[57] ABSTRACT

To avoid the formation of acidity in an F125 containing olefins, a radical scavenger and/or an acidity scavenger is added to it.

2 Claims, No Drawings

PROCESS FOR STABILIZATION OF PENTAFLUOROETHANE

FIELD OF THE INVENTION

The present invention relates to the field of HFCs (hydrofluorocarbons) and its subject-matter is more particularly a process for stabilization of pentafluoroethane, known in the trade under the designation F125 and the main field of application of which, as a substitute for CFCs, is low-temperature refrigeration.

BACKGROUND OF THE INVENTION

Access to F125 is possible by various routes described in the literature, such as the fluorination of perchloroethylene or of one of its fluoro derivatives and the hydrogenolysis of pentachloroethane (F115). Pure F125 is a completely stable compound which does not undergo any transformation or decomposition in the normal conditions of synthesis, storage and use (T<500° C.). However, it is not easy to obtain an F125 of high purity and, regardless of the method of synthesis employed, the product contains, as main impurities, not only F115 but also various olefins which are more or less toxic and which, especially chlorotrifluoroethylene (F1113), are difficult to separate from F125.

Product purity specifications for F125 have been established from the toxicological study of F125 carried out as part of the PAFTT III (Program for Alternative Fluorocarbon Toxicity Testing). In the case of most of the olefins (F1111, F1113, F1114, etc), the specification for each of these is set according to its toxicity at a content of between 0 and 1000 ppm. Thus, in the case of the highly toxic olefins like PFIB (perfluoroisobutene), the permitted concentration is well below one ppb. Conversely, in the case of less toxic olefins, the specification is much less severe and can be up to several hundred ppm.

These specifications with regard to olefins are generally easy to meet when conventional processes for the synthesis of F125 (fluorination, hydrogenolysis) are employed. However, some of these olefins are difficult to separate from F125 merely by distillation, which is why their presence, and especially that of F1113, is often noted in the commercial products. At the present time, according to the suppliers, commercial F125 exhibits an F1113 content which oscillates between 5 and 90 ppm, in most cases between 20 and 80 ppm.

Until now the stabilization of HFCs has not seemed necessary and there has been concern only with that of the HCFCs (hydrochlorofluorocarbons) like 1,1- dichloro-1-fluoroethane (F114b) and 1,1-dichloro-2,2,2-trifluoroethane (F123). Thus, the stabilization of F141b containing traces of 1,1-dichloroethylene (F1130a) by means of an ethylenic hydrocarbon containing at least 4 carbon atoms has been described in patent FR 2 682 377; the use of α-methylstyrene or of nitromethane for stabilizing F141b is claimed in patent EP 539 719. To inhibit the degradation of F123 and/or of F123a when used in foams in the presence of polyols, patent EP 508 449 recommends the addition of nitrostabilizers like nitromethane. Application WO 92/17559 claims the stabilization of F123 by means of a phenol, of an aromatic compound or of an epoxide.

DESCRIPTION OF THE INVENTION

It has now been found that some of the olefins present in low concentrations in a commercial F125 can decompose in the presence of oxygen. This decomposition can take place even in very mild conditions which are comparable with the usual conditions of storage or use of F125 (ambient temperature, closed system) and is reflected in the presence of acidity resulting in an F125 out of specification.

To avoid the formation of acidity and thus to limit the risks of damage to the equipment operating with refrigerant mixtures based on F125, the total removal of the olefins in the F125 is a priori a tempting solution; however, the total removal of the F1113 in F125 by distillation is difficult or even impossible. The "zero olefin" objective for F125 can therefore be attained only at the price of a costly additional purification stage, since it is necessary to resort to chemical treatments or to physical purifications.

According to the present invention this problem is solved by adding to an F125 containing olefins a sufficient quantity of at least one radical scavenger and/or an acidity scavenger. It has been found, in fact, that this addition allows an F125 to be stabilized durably and inexpensively.

The addition of a radical scavenger which blocks the radical chain reactions makes it possible to avoid the decomposition of the olefins. Furthermore, the addition of an acidity scavenger prevents the decomposition reaction from autoaccelerating with the formation of acidity. In this way the F125 remains at a neutral pH and the decomposition of the olefins which are present, especially of F1113, is minimal, or even nil.

Molecules containing a system of conjugated double bonds, such as, for example, aromatic compounds, dienes and pyrrole derivatives can be employed as radical scavengers, no limitation being implied. As nonlimiting examples of such compounds there may be mentioned styrene, α-methylstyrene, phenol, 4-methoxyphenol (EMHQ), butadiene, isoprene, 3-methyl-1,2-butadiene, 1,3-pentadiene, terpenes and N-methylpyrrole.

The acidity scavenger can, without any limitation being implied, be chosen from amines and epoxides. Examples of amines which may be mentioned are triethylamine and tributylamine, and examples of epoxides are butylene oxide and 1,2-epoxyhexane.

Among the abovementioned stabilizers it is preferable to employ more particularly α-methylstyrene, butylene oxide, triethylamine, tributylamine, isoprene or EMHQ.

The quantity of stabilizer to be added to the F125 quite obviously depends on the content of olefinic impurities in the F125 to be treated. The proportion of stabilizer can therefore range from some tens of ppm to several per cent. A quantity of stabilizer is generally added which, expressed in molar equivalents, corresponds to a ratio of stabilizer to the olefins present in the F125 of between 0.05 and 5, preferably between 0.1 and 2. Thus, in the case of a commercial F125 in which the total olefin content is generally much lower than 500 ppm by weight, the addition of 0.1% by weight of stabilizer is found to be amply sufficient.

The stabilizer can be introduced into the F125 either directly into the storage tanks of the production unit or during the packaging. To avoid any risk of decomposition the storage tanks are blanketed with inert gas and it is preferable to introduce the stabilizer(s) already when these tanks are being filled.

EXAMPLES

The following examples illustrate the invention without limiting it.

EXAMPLES 1 to 8

Into a sealed tube (volume: 8 ml) are introduced 1.5 g of F125, 500 ppm of F1113, the quantity of stabilizer shown in the table (except for Examples 6 and 7, carried out without stabilizer) and air in a proportion of 5 mol % relative to the F125 (except for Example 7, carried out without air and without stabilizer).

Each tube is stored at 80° C. for 48 hours. After this time interval the sealed tube is cooled to liquid nitrogen temperature and brought into communication with a previously evacuated steel bottle (volume: 20 ml) maintained at the temperature of liquid nitrogen. The top of the tube is then broken and the tube is gently heated to the ambient temperature, to recover the gases by trapping in the metal test tube.

1.5 g of the gas are thus recovered in the test tube and then analysed by gas chromatography. The results are listed in the following table.

Examples 1 to 5 show that the presence of a stabilizer inhibits the decomposition of F1113 and the appearance of acidity, and does so despite the fairly severe conditions (80° C.). Example 6 shows that the addition of a stabilizer is necessary and Example 7 that air is responsible for the decomposition of the olefins and for the appearance of acidity.

| EXAMPLE | AIR % | STABILIZER Name | Quantity | F1113 CONTENT AFTER THE TEST |
|---|---|---|---|---|
| 1 | 5 | butylene oxide | 0.7 mg 466 ppm | 500 ppm |
| 2 | 5 | α-methylstyrene | 0.6 mg 400 ppm | 500 ppm |
| 3 | 5 | tributylamine | 0.8 mg 533 ppm | 500 ppm |
| 4 | 5 | triethylamine | 0.4 mg 266 ppm | 500 ppm |
| 5 | 5 | EMHQ | 0.3 mg 2.00 ppm | 500 ppm |
| 6 comparative | 5 | none | — | 40 ppm |
| 7 comparative | 0 | none | — | 500 ppm |
| 8 comparative | 5 | nitromethane | 0.3 mg 200 ppm | 400 ppm |

EXAMPLES 9 AND 10

A commercial F125 containing only 14 ppm of F1113 was stored for 30 days at ambient temperature and in the presence of air (5% by volume relative to F125).

25 ppm of triethylamine were added to the F125 in Example 9, whereas Example 10 was carried out with an F125 containing no stabilizer.

After 30 days' storage the stabilized F125 (Example 9) showed no change in the material whereas, in the case of that in Example 10, a decrease in the F1113 content (a change from 14 ppm to 1 ppm) and the appearance of acidity (16.5 mg/l expressed as HCl) were observed.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for stabilization of an impure pentafluoroethane (F125) containing olefins, which are difficult to separate, comprising adding an effective quantity of at least one radical scavenger and/or an acidity scavenger to the F125 containing at least one perhalogenated olefin or chlorotrifluoroethylene (F1113); the quantity, expressed in molar equivalents, corresponds to a stabilizer/olefins ratio of between 0.05 and 5; the radical scavenger is selected from α-methylstyrene, 4-methoxyphenol, isoprene, 1,2-expoxyhexane, styrene, phenol, 1,2-butadiene, 1,3-pentadiene, terpene and N-methylpyrrole; the acidity scavenger is selected from triethylamine, tributylamine and butylene oxide; whereby formation of acidity is substantially avoided.

2. Process according to claim 1, wherein the ratio is between 0.1 and 2.

* * * * *